(12) United States Patent
Harper

(10) Patent No.: US 11,041,860 B2
(45) Date of Patent: Jun. 22, 2021

(54) POINT-OF-CARE DEVICE FOR THE COLORIMETRIC DETERMINATION OF HEMOGLOBIN AND GLUCOSE-6-PHOSPHATE DEHYDROGENASE IN BIOLOGICAL SAMPLES

(71) Applicant: ANALYTICAL DIAGNOSTIC SOLUTIONS, INC., Mount Laurel, NJ (US)

(72) Inventor: Robert Harper, Mount Laurel, NJ (US)

(73) Assignee: ANALYTICAL DIAGNOSTIC SOLUTIONS, INC., Mount Laurel, NJ (US)

( * ) Notice: Subject to any disclaimer, the term of this patent is extended or adjusted under 35 U.S.C. 154(b) by 118 days.

(21) Appl. No.: 16/084,700

(22) PCT Filed: Mar. 20, 2017

(86) PCT No.: PCT/US2017/023153
§ 371 (c)(1),
(2) Date: Sep. 13, 2018

(87) PCT Pub. No.: WO2017/161363
PCT Pub. Date: Sep. 21, 2017

(65) Prior Publication Data
US 2019/0072553 A1 Mar. 7, 2019

Related U.S. Application Data

(60) Provisional application No. 62/310,273, filed on Mar. 18, 2016.

(51) Int. Cl.
*G01N 33/573* (2006.01)
*G01N 33/52* (2006.01)
*G01N 33/558* (2006.01)

(52) U.S. Cl.
CPC ......... *G01N 33/573* (2013.01); *G01N 33/526* (2013.01); *G01N 33/558* (2013.01); *G01N 2333/805* (2013.01); *G01N 2333/902* (2013.01); *Y02A 50/30* (2018.01)

(58) Field of Classification Search
CPC . A23J 3/345; A61B 5/14507; G01N 21/8483; G01N 33/48; G01N 33/483; G01N 33/487; G01N 33/52; G01N 33/573; G01N 33/558; G01N 33/526; G01N 2333/805; G01N 2333/902; Y02A 50/58; Y02A 50/30
USPC .......................................................... 435/26
See application file for complete search history.

(56) References Cited

U.S. PATENT DOCUMENTS

| | | | | |
|---|---|---|---|---|
| 5,223,219 | A * | 6/1993 | Subramanian | B01L 3/5027 210/451 |
| 6,524,864 | B2 * | 2/2003 | Fernandez Decastro | G01N 33/526 422/400 |
| 7,887,750 | B2 * | 2/2011 | Blatt | B01L 3/5027 422/423 |
| 2005/0214161 | A1 * | 9/2005 | Gupta | G01N 33/5091 422/400 |
| 2013/0022969 | A1 * | 1/2013 | Kim | G01N 33/523 435/6.1 |
| 2013/0224781 | A1 * | 8/2013 | Jung | A61B 5/1468 435/26 |
| 2015/0192512 | A1 | 7/2015 | Srivastava | 436/66 |

FOREIGN PATENT DOCUMENTS

| WO | WO 2016/040620 | | 3/1916 | |
|---|---|---|---|---|
| WO | WO-2016040620 A1 * | | 3/2016 | ........... G01N 33/721 |

OTHER PUBLICATIONS

International Search Report and Written Opinion in PCT/US2017/023153 dated Jun. 21, 2017.
International Preliminary Report on Patentability in PCT/US2017/023153 dated Sep. 18, 2018.

* cited by examiner

*Primary Examiner* — Satyendra K Singh
(74) *Attorney, Agent, or Firm* — Licata & Tyrrell P.C.

(57) ABSTRACT

Devices, kits, and assays are provided for the testing and monitoring of hemoglobin, anemia, glucose-6-phoshate dehydrogenase, and glucose-6-phosphate dehydrogenase deficiency in an individual.

9 Claims, 9 Drawing Sheets

POINT-OF-CARE DEVICE FOR THE COLORIMETRIC DETERMINATION OF HEMOGLOBIN AND GLUCOSE-6-PHOSPHATE DEHYDROGENASE IN BIOLOGICAL SAMPLES

This patent application is the National Stage of International Application No. PCT/US2017/023153, filed Mar. 20, 2017 which claims the benefit of priority from U.S. Provisional Patent Application Ser. No. 62/310,273, file Mar. 18, 2016, the contents of which are incorporated herein by reference in their entirety.

FIELD OF THE INVENTION

The present invention relates to devices, kits, and assays for the testing and monitoring of hemoglobin levels and anemia, as well as glucose-6-phoshate dehydrogenase levels and glucose-6-phosphate dehydrogenase deficiency in an individual.

BACKGROUND OF THE INVENTION

The enzyme glucose-6-phosphate dehydrogenase ("G6PD") performs a critical function in human biochemistry. It is part of the oxidative pentose pathway, wherein it functions to minimize the oxidative attacks of free radicals upon cells by providing reducing equivalents, (i.e. G6PD converts glucose-6-phosphate to 6-phosphoglutonate) thereby liberating a proton that reduces nicotinamide adenine dinucleotide phosphate (NADP$^+$) to NADPH. The NADPH initiates a series of downstream reactions that ultimately reduce the free radical oxidizing agents, rendering many of them ineffective in normal human biochemistry.

Malaria caused by *Plasmodium vivax* threatens over 2 billion people globally and sickens tens of millions annually. Most acute attacks by this species derive from latent forms in the human liver called hypnozoites. The radical treatment for *P. vivax* malaria includes therapy aimed both at the acute attack (blood schizontocidal) and against future attacks (hypnozoitocidal). Currently, the only hypnozoitocides available are 8-aminoquinolines such as primaquine. However, clinicians are hesitant to, and often do not, prescribe primaquine due to the high prevalence (8%) of individuals with inherited Glucose-6-phosphate dehydrogenase (G6PD) deficiency which affects 400 million people worldwide. Unfortunately, primaquine can cause life-threatening acute hemolytic anemia in patients with G6PD deficiency. Moreover, given the high number of genetic mutant variants (>300), it is not currently possible to screen patients who contract malaria for G6PD mutations. As a result, clinicians choose not to treat malaria caused by *Plasmodium vivax* to avoid the lethal risk of primaquine for what was perceived as a non-threatening infection. However, recent clinical evidence now discredits the long-held notion of this infection as intrinsically benign, revealing an often life threatening course associated with mortality. Because of this, there is a critical need to develop point-of-care diagnostic tools to help identify G6PD deficient individuals so that patients who can tolerate and cannot tolerate primaquine treatment can be identified.

The availability of a point-of-care G6PD diagnostic kit that could be used in the rural tropical areas most affected by malaria would both protect the individuals vulnerable to primaquine therapy and enable the "normal-G6PD" majority to receive curative treatments. This would also prevent repeated clinical attacks and reduce further transmission of the hypnozoites throughput the population.

SUMMARY OF INVENTION

An aspect of the present invention relates to a test strip that can simultaneously determine glucose-6-phosphate dehydrogenase (G6PDH) and hemoglobin (Hgb) in a biological sample.

Another aspect of the present invention relates to a new diagnostic kit and assay for the colorimetric analysis and quantitative determination of hemoglobin (Hgb) and glucose-6-phosphate dehydrogenase (G6PDH) in biological specimens. The kit and assay comprise a combination of components which elicit a colored end-product of both Hgb and a specific enzymatic reaction for G6PDH, which is either absent, insufficiently present, or in excess in the biological sample. In one non-limiting embodiment, the kit and assay use the test strip for simultaneously determining glucose-6-phosphate dehydrogenase (G6PDH) and hemoglobin in a biological sample. In one non-limiting embodiment, the kit and assay only require 30 µL from a fingerstick sample or blood from a collection vessel. Red blood cells are lysed, liberating both free Hgb and the enzyme G6PDH, both of which are quantitatively determined colorimetrically using, for example, a reflectance-based reader, a photometric imager, or electrochemical detection. A ratiometric determination of Hgb (g/dL) and units G6PDH can then be calculated as (Units G6PDH)/(g/dL Hgb). The kit and assay can be based on end-color signal or kinetic determination. This assay is quantitative, faster, sturdier, and easier to perform than analogous wet chemistry assays and lateral flow assays. In the long term, the kit can be used as a point-of-care monitoring test with, for example, a fingerstick blood sample analogous to glucose testing and can be performed and monitored by either the patient or the clinician.

Another aspect of the present invention relates to methods for identifying individuals in need who can tolerate and cannot tolerate primaquine treatment with these kits and assays.

DETAILED DESCRIPTION OF THE INVENTION

The present invention provides kits and assays for the simultaneous determination of hemoglobin concentration and units of G6PDH in a biological fluid, including but not limited to whole blood, saliva, and urine.

Figure 3:
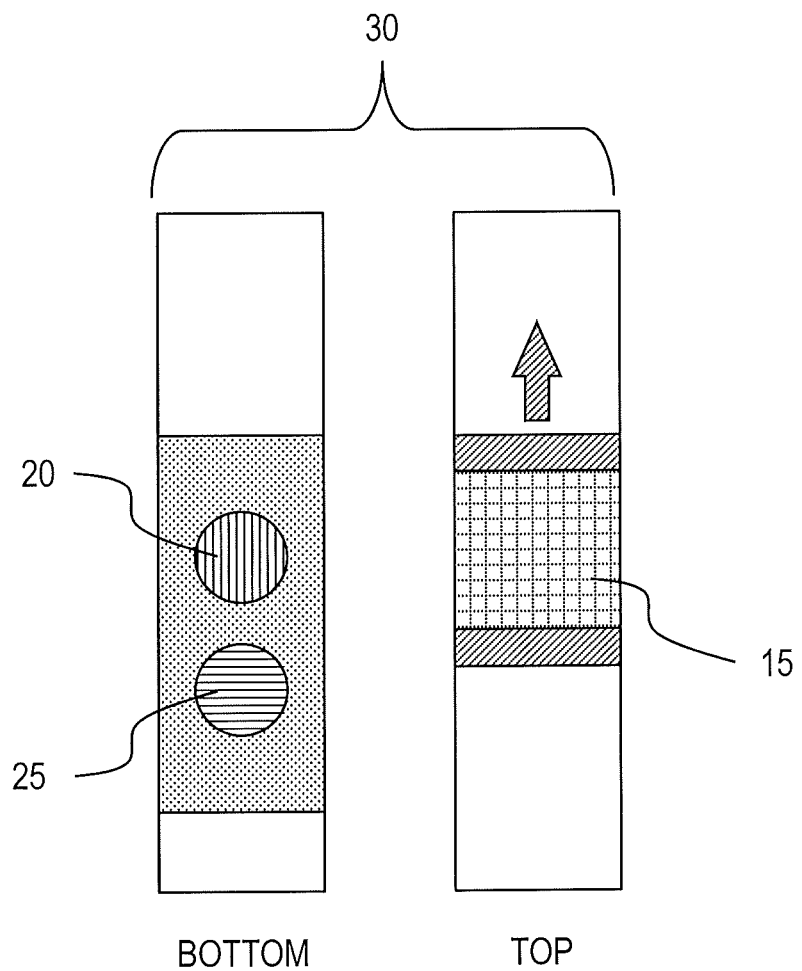
FIG. 3 is a diagram of a non-limiting embodiment of a test strip showing a top portion with the sample collection pad and a bottom portion with hemoglobin reagent and G6PDH reagent membranes.

In one non-limiting embodiment, a test strip is used comprising of at least three superimposed membrane layers. A diagram of one non-limiting embodiment of a test strip 30 of the present invention showing the top portion of the test strip with the sample collection pad 15 and the bottom portion with a hemoglobin reagent membrane 20 and G6PDH reagent membrane 25 is depicted in FIG. 3. In one non-limiting embodiment, the membrane layers can be adhered to a base material made of, for example, polyester through lamination with pressure sensitive adhesives. In another non-limiting embodiment, the membrane layers are superimposed without lamination or an adhesive into a clamshell design. The clamshell may be comprised of a pliable polyester or a rigid plastic housing. The top of the clamshell folds over and clasps onto the base layer, which holds the membranes in place.

The test strip, comprised of multiple, stacked membranes, provides a detectable, quantitative change in response to the concentration of Hgb and G6PDH present in the biological sample applied to the strip. In one embodiment, the biological sample is whole blood from, for example, a fingerstick sample.

The test strip comprises a sample spreading layer. The sample spreading layer is capable of distributing or metering the red and white blood cells across the surface of a primary membrane. The spreading layer provides a uniform concentration of the cells at the interface of the spreading layer and the primary membrane. Accordingly, precise permeability of the spreading layer is critical to providing uniform distribution of the biological sample across the surface of the primary membrane layer. Examples of materials for the spreading layer include, but are not limited to, hydrophilic mesh materials, isotropically porous materials (same porosity throughout), and anisotropic membranes (having a gradient in porosity) of varying pore sizes. In one non-limiting embodiment, the spreading layer comprises an anisotropic membrane with a ratio of pore size ranging from, for example, 100 µm to 1 µm or from 10 µm to 0.1 µm. The surface of the spreading layer must be in direct contact with the primary membrane for uniform transfer of the biological material.

A biological fluid applied to the test strip flows transversely across the spreading layer and then migrates vertically into the primary membrane. The primary membrane is a digestive membrane. The digestive membrane can be one of several membranes including, but not limited to, glass fiber, nylon, cellulose, or polyethersulfone. The primary membrane is further comprised of one or more hemolytic agents including, but not limited to, surfactants or salts such as Triton X-100, sodium cholate, benzalkonium chloride, ammonium chloride, and saponin. In one non-limiting embodiment, one or more hemolytic agents are immobilized with a mordant such as, but not limited to, hydroxypropyl cellulose, hydroxyethyl cellulose, sodium carboxymethyl cellulose, polyvinyl alcohol, xanthan gum, and hydrogels.

The hemolyzed sample is then vertically or horizontally fed into the secondary membranes of the test strip. For purposes of the present invention, the Hgb secondary membrane is referred to herein as Membrane 2A and the secondary membrane for the G6PDH assay is referred to herein as Membrane 2B. Membrane 2A is not in direct contact with Membrane 2B.

In one nonlimiting embodiment, Membrane 2A comprises a surfactant, an immobilizing mordant, sodium azide, and sodium nitrite or an oxidizing agent to convert $Fe^{(2+)}$ to $Fe^{(3+)}$. Membrane 2A can be comprised of but not limited to: nylon, polyester, glass fiber, polysulfone, or polyethersulfone. This membrane can be either isotropic or anisotropic. Examples of mordants include, but are not limited to, hydroxypropyl cellulose, hydroxyethyl cellulose, sodium carboxymethyl cellulose, polyvinyl alcohol, xanthan gum, and hydrogels. The biological fluid slowly migrates vertically or horizontally as per the above teaching from the primary membrane into the secondary membrane, Membrane 2A. The hemoglobin becomes oxidized by the sodium nitrite or oxidizing agent to form methemoglobin. Methemoglobin complexes with sodium azide to form azidomethemoglobin. The end-color intensity of the azidomethemoglobin can be read colorimetrically.

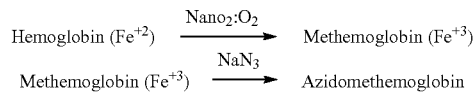

The end-color intensity can be read as reflectance units and converted to g/dL through a curve set against a laboratory reference instrument or as an optical image obtaining red, blue, green (RBG) values or pixel count which can then be calibrated against a laboratory reference instrument.

Membrane 2B comprises a surfactant, mordant, substrate (glucose-6-phosphate), and sodium nitrite. The biological fluid slowly migrates vertically or horizontally as per the above teaching from the primary membrane into the secondary membrane, Membrane 2B. Membrane 2B can be comprised of but not limited to: nylon, polyester, glass fiber, polysulfone, and polyethersulfone. This membrane can be either isotropic or anisotropic. The biological fluid is pre-conditioned with a buffering system and sodium nitrite which are immobilized to the membrane by a mordant. Membrane 2B contains a buffer and a pH in the range of 7.0-9.0. The pre-conditioning of the biological fluid allows for homogenous mixing of the substrate and buffer in order to adjust the biological sample to an optimal pH to accelerate the completion of the reaction and increase the rate of the reaction. The components in Membrane 2B are immobilized with a mordant. Examples of mordants include, but not limited to, hydroxypropyl cellulose, hydroxyethyl cellulose, sodium carboxymethyl cellulose, polyvinyl alcohol, xanthan gum, and hydrogels.

The sample is then vertically or horizontally fed into the tertiary membranes of the test strip. For purposes of the present invention, the Hgb tertiary membrane is referred to herein as Membrane 3A, and the tertiary membrane for G6PDH is referred to herein as Membrane 3B. Membrane 3A is segregated from or horizontal to Membrane 3B.

The hemolyzed fluid containing azidomethemoglobin travels from Membrane 2A to Membrane 3A. Membrane 3A contains a surfactant. The biological fluid slowly migrates vertically or horizontally from Membrane 2A into Membrane 3A. The tertiary membrane is an "optical" membrane. The optical membrane removes small particulate cellular debris and provides a uniform color across the surface of the membrane, providing a consistent end-color in the "read zone" for precise detection.

The buffered hemolyzed fluid containing the substrate, glucose-6-phosphate, travels from Membrane 2B to Membrane 3B. Membrane 3B comprises a surfactant, an electron mediator such as, but not limited to, diaphorase or 1-methoxy-5-methylphenazinium methylsulfate (1-methoxy PMS), $NADP^+$, and an indicator such as, but not limited to, a tetrazolium salt. Membrane 3B further comprises bioreactive incipients, generating signal (color) which is proportional to the liberated G6PDH. The Membrane 3B end-color intensity or kinetic rate determination of color development is proportional to the units of G6PDH in the biological sample.

G6PDH catalyzes the oxidation of D-glucose-6-phosphate (G-6-P) to 6-phospho-D-glucono-1,5-lactone (6-PG) and reduces NADP⁺ to NADPH.

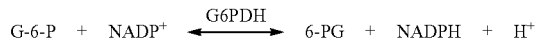

In the presence of an electron mediator, such as diaphorase or 1-methoxy PMS, and an indicator such as a tetrazolium salt, the end color intensity or rate of color development is proportional to the G6DPH concentration.

Suitable electron mediators include diaphorase, which can be used in the reduction of tetrazolium salts. In addition, non-enzymatic electron transfer agents such as phenazine methosulfate (PMS), phenazine ethosulfate (PES), 1-methoxy-5-methylphenazinium methyl sulfate (1-methoxy PMS), or 8-Dimethylamino-2,3-benzophenoxazine hemi(zinc chloride) salt (Meldola's Blue) can be used. In one non-limiting embodiment, diaphorase is used in tandem with 1-methoxy-5-methylphenazinium methyl sulfate (1-methoxy PMS). Reaction kinetics and stability are the primary factors for selecting an electron mediator or "hydride abstractor". For example, PMS is a universal hydride abstractor, because it has relatively fast reaction kinetics with most tetrazolium compounds. PMS is, however, more sensitive to light than enzyme-based hydride abstractors. Diaphorase is more stable and, for that reason, is the preferred electron mediator to be used in addition to the cofactor NADP⁺.

In one non-limiting embodiment, the optical and reagent membranes are positioned over 2 LEDs with wavelengths for detection of analytes both between 400 and 700 nm to read the color intensity of both analytes by reflectance determination via a reflectance meter.

Figure 4A:
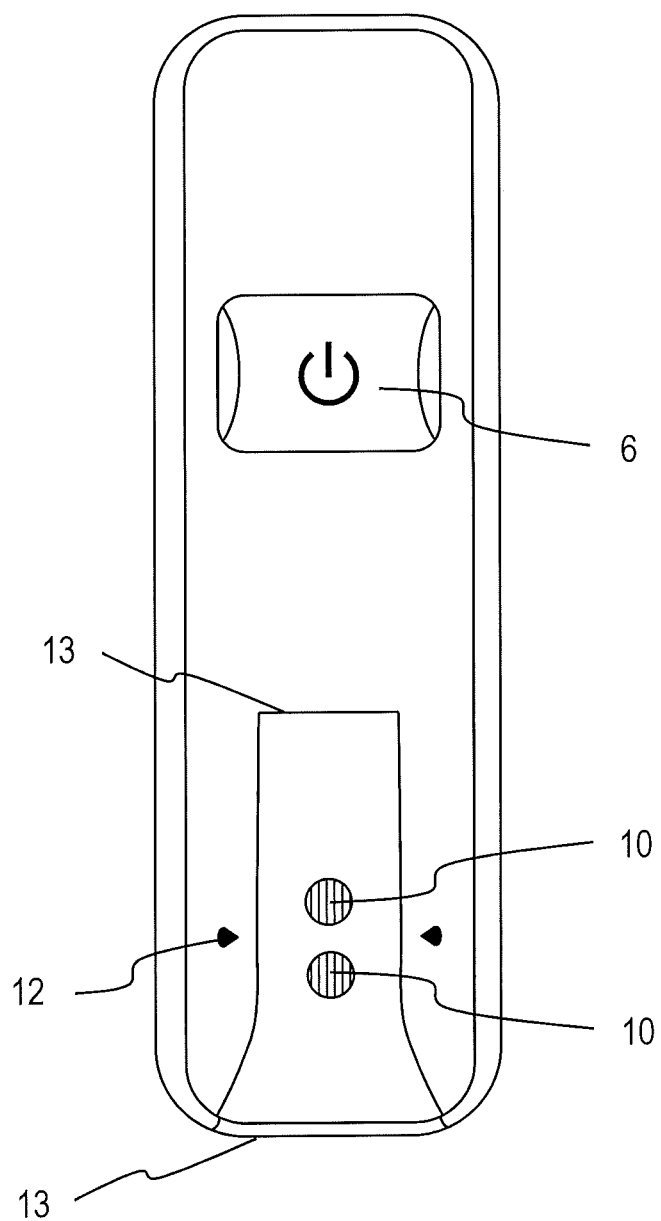
FIGS. 4A and 4B shows a non-limiting embodiment of an outer cover of a test meter with an insertion channel (see FIG. 4A) into which a test strip of the present invention can be inserted (see FIG. 4B).
Figure 4B:
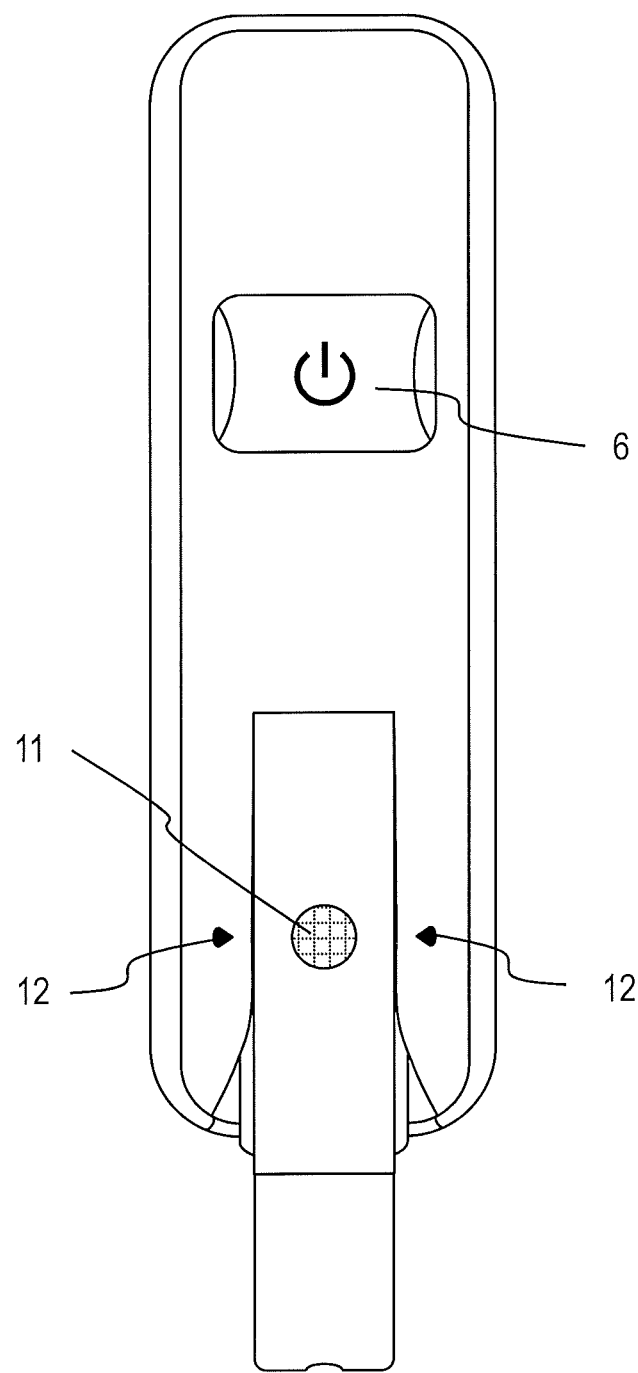
Figure 5A:
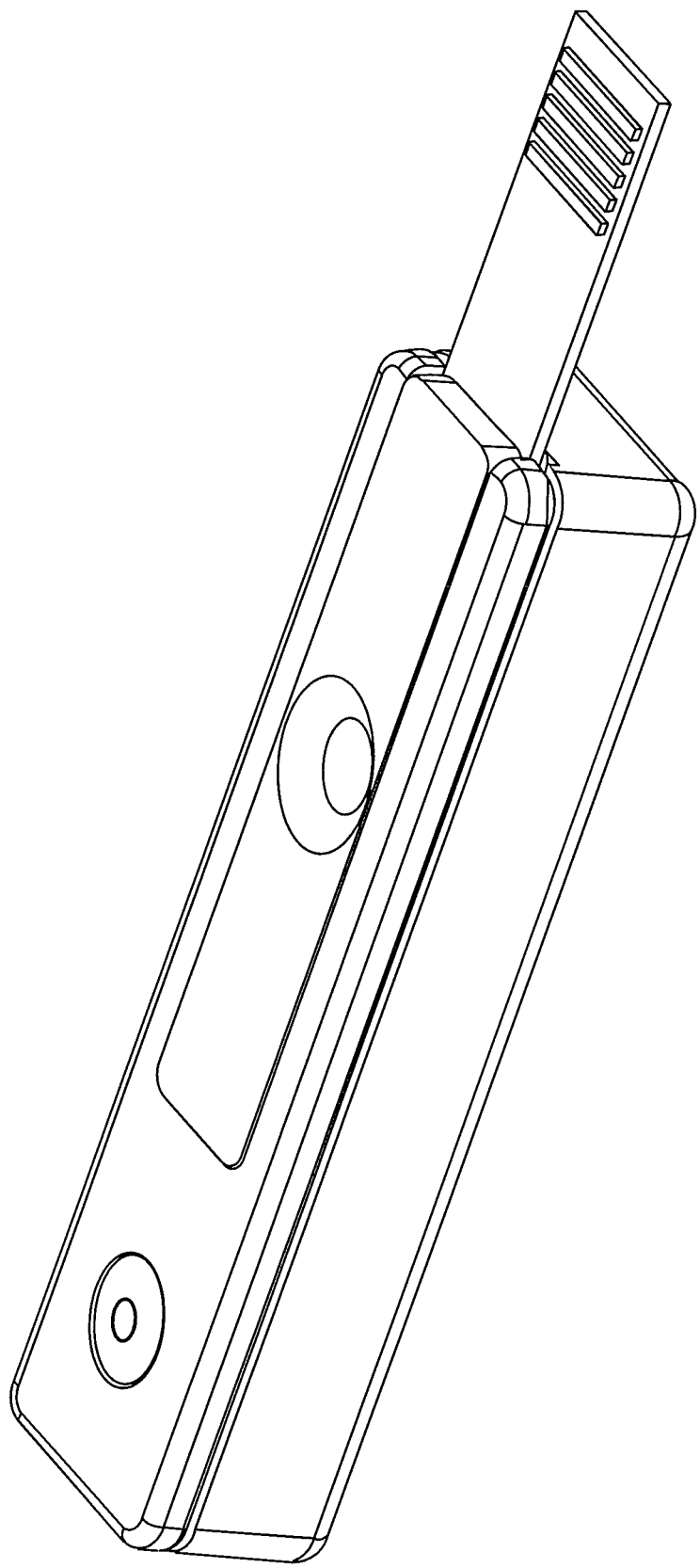
FIG. 5A through 5E are diagrams depicting components of a non-limiting embodiment of a test meter inclusive of the outer cover and case (see FIGS. 5A, 5C, and 5E) as well as the inner meter components (see FIGS. 5B and 5D).
Figure 5B:
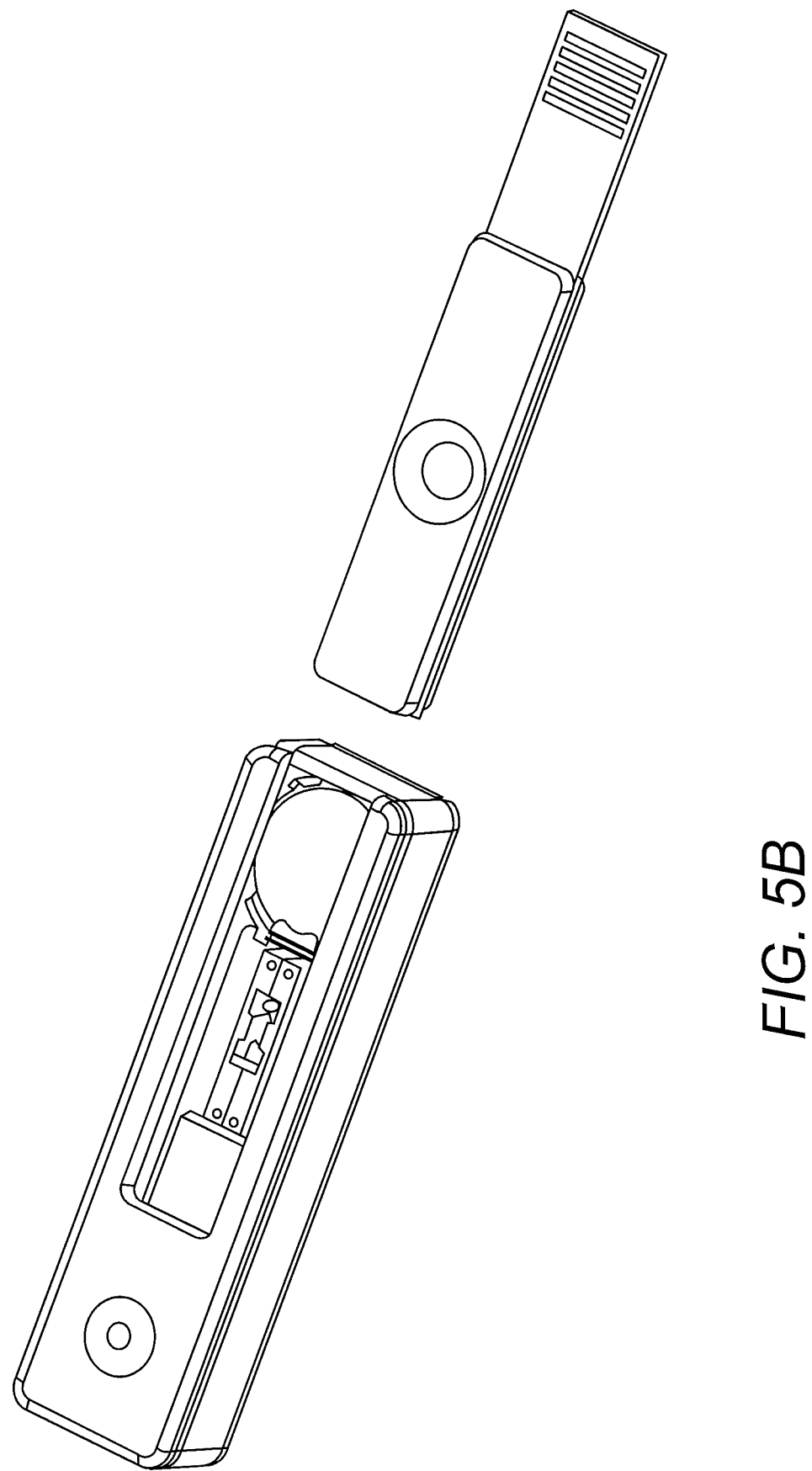
Figure 5C:
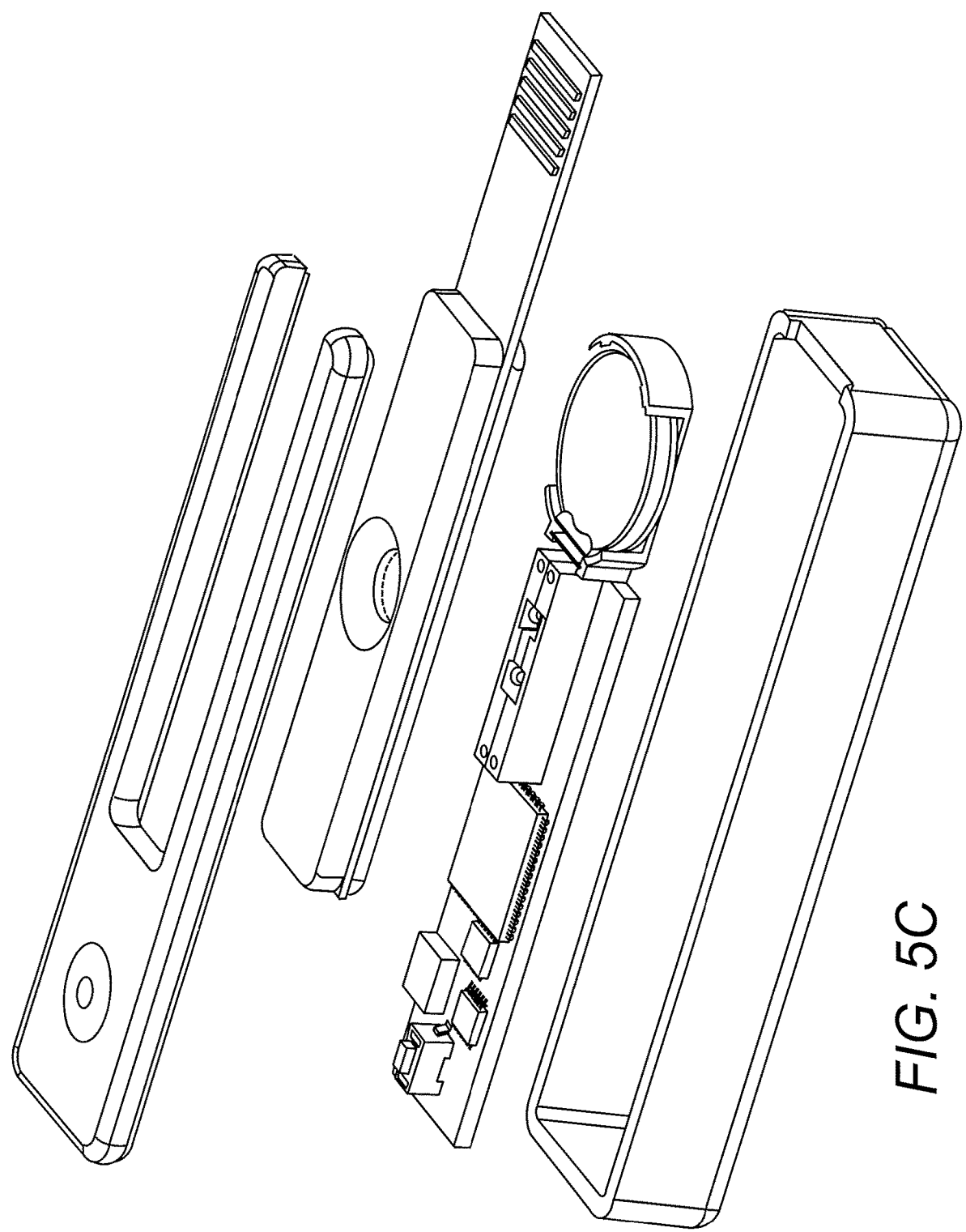
Figure 5D:
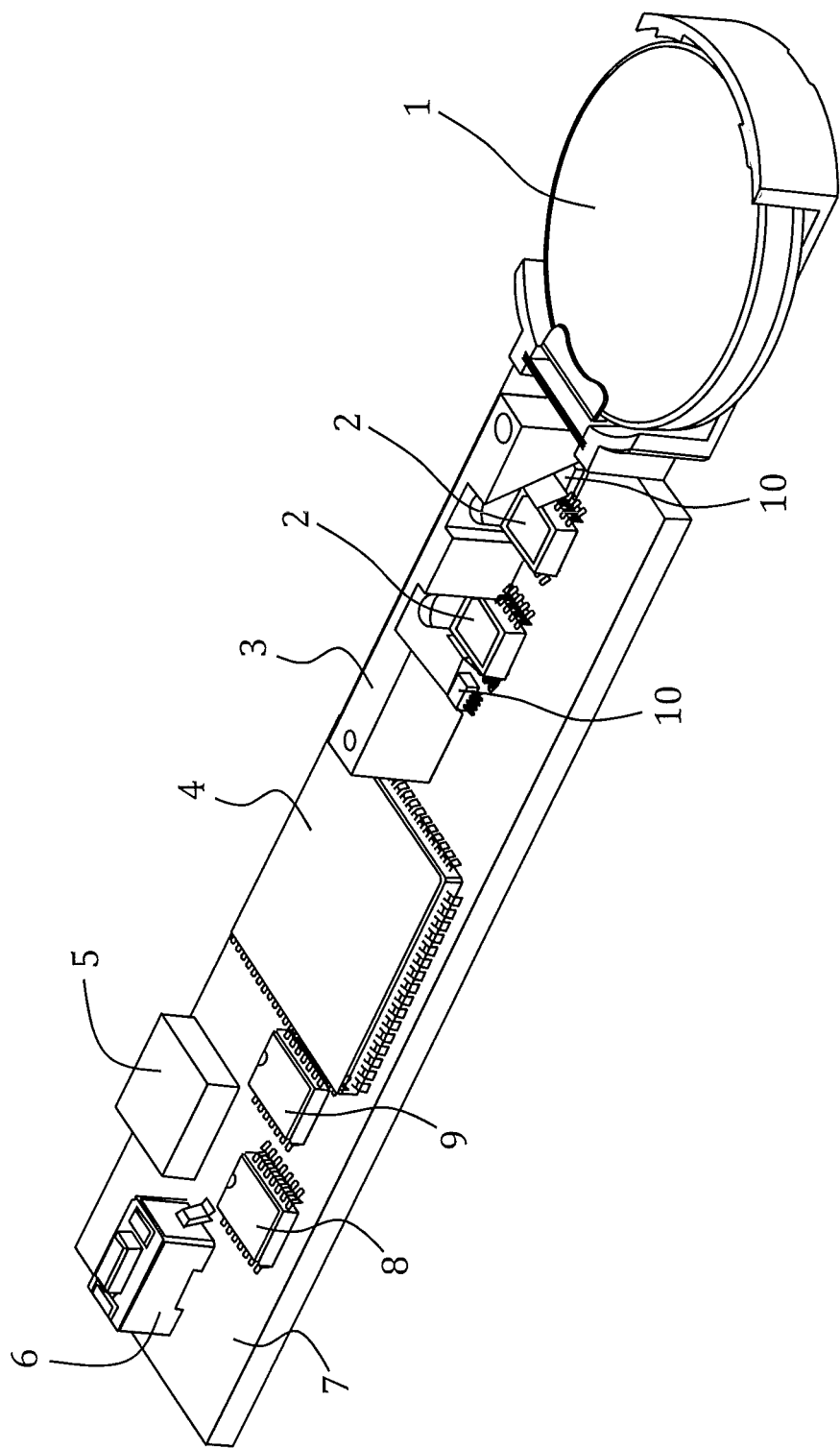
Figure 5E:
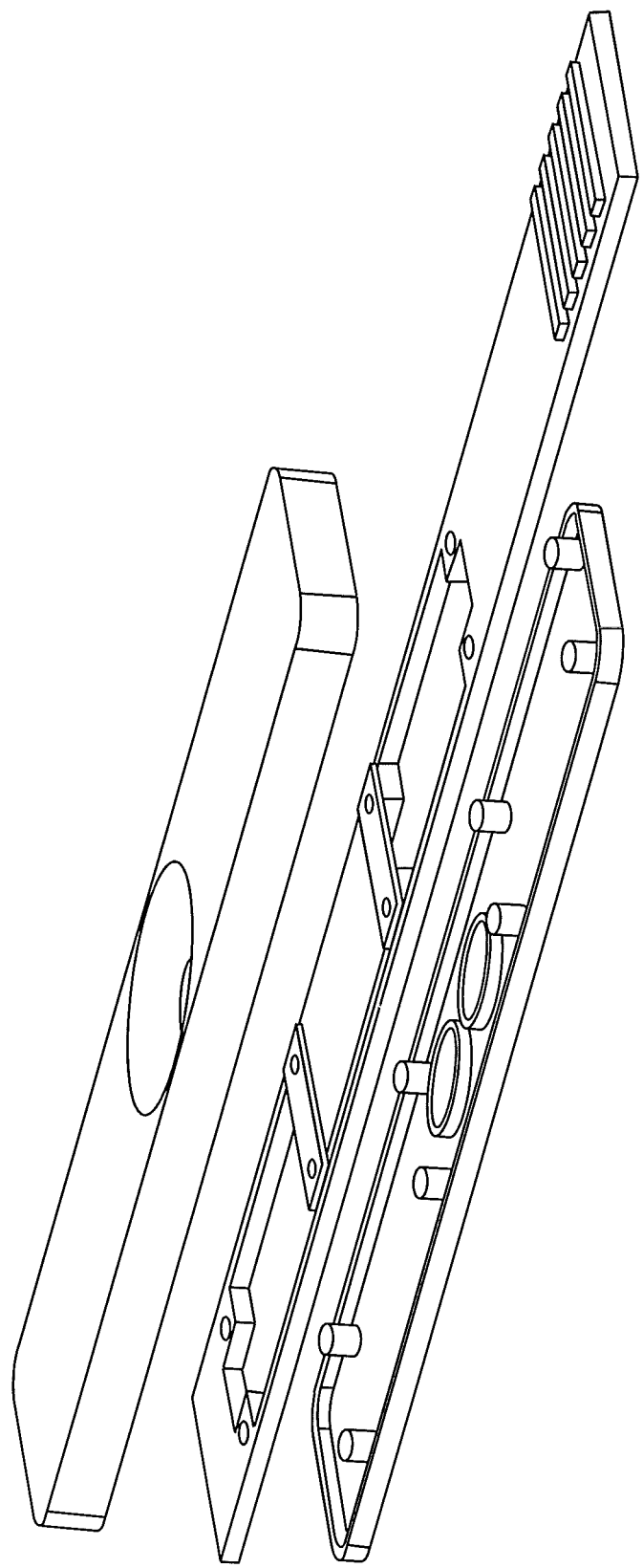

One non-limiting embodiment of an LED-based test meter into which a test strip of the present invention can be inserted is depicted in FIGS. 4A and 4B, as well as in FIG. 5A-5E. FIGS. 4A and 4B show one non-limiting embodiment of a outer cover of the test meter (see FIG. 4A) with an insertion channel 13 for insertion of the test strip 30, a power button 6, green and red LEDs 10 for reading of the hemoglobin membrane and the G6PDH membrane, and in FIG. 4B a sample application well 11 with sample well alignment arrows 12. FIG. 5A through 5E provide a diagram of the various components of this non-limiting embodiment of a test meter inclusive of the outer cover and case (see FIGS. 5A, 5C, and 5E) as well as the inner meter components comprising a battery 1, a photodectector I.C. 2, a light guide 3, a microcontroller with memory 4, a BLUETOOTH transceiver I.C. 5, a power button 6, a printed circuit board 7, a power conditioning I.C. 8, an analog to digital converter 9 and green and red LED lights 10 (see FIGS. 5B and 5D).

In another non-limiting embodiment, the optical and reagent membranes are positioned over a camera to image the end color development using RBG values or pixel count via a photometric metric image. The meter or camera contains software which quantifies (Units G6PDH)/(grams/dL Hgb) multiplied by a temperature correction factor. Using an algorithm, the meter or camera can compensate for rate changes due to changes in testing temperatures.

In one nonlimiting embodiment, the test meter transmits measured data to a mobile application on, for example, a cell phone, tablet or computer.

The 'normal' range for blood Glucose-6-Phosphate Dehydrogenase is 9.9-16.6 Units G6PDH/(gram/dL Hgb) (ARUP labs). The assays and kits of the present invention provide an analytical range of 0.03 to 25.0 Units G6PDH/(gram/dL Hgb). This range exceeds the "gold standard" G6PDH test manufactured by Trinity Biotech. The "gold standard" G6PDH reference levels were designated by the international nonprofit organization PATH.

The 'normal' range for blood Hgb is 12-18 g/dL Hgb. The assays and kits of the present invention provide an analytical range of 3.0 to 24.0 g/dL Hgb.

In practice, the test strips, kits, and assays of the present invention determine both hemoglobin levels and G6PDH levels as a point-of-care test. This is a critical application. Both concentrations of Hgb and G6PDH are critical parameters for the pre- and post-assessment in dietary restrictions, the administration of analgesics, the diagnosis of G6PDH deficiency, and the monitoring of both Hgb and G6PDH during the treatment malaria. The test strips, kits, and assays of this invention can be used for both initial diagnostic determination of the genetic disorder of G6PDH deficiency and for monitoring purposes. This includes patients on restricted diets as well as those receiving medication, including analgesics or other drugs for the therapeutic treatment of malaria. The test strips, kits, and assays of the present invention also determine an anemic patient's Hgb level, which is essential in providing a critical data in the pre- and post-administration of anti-malaria medications. The assay can be performed with a volume of blood from a fingerstick, which is approximately 30 μL. This allows an ease-of-use for the patient, especially for those using the test strips, kits, and assays in more rural settings.

Calibration standards for both Hgb and G6PDH can be obtained by spiking and/or modifying whole blood samples, or by purchasing cryogenically preserved reference samples. All samples are sent out to reference laboratories to validate Hgb values (g/dL) and units G6PDH. Samples of known reference values are assayed with the test strips and the percent reflectance for each sample is recorded. These samples will encompass the analytical range of both anemic and G6PDH deficient patients. The G6PD variants and diagnosis have been divided into 5 classes according to the level of enzyme activity: Class 1-enzyme deficiency with chronic nonspherocytic hemolytic anemia; Class 2-severe enzyme deficiency (less than 10%); Class 3-moderate to mild enzyme deficiency (10-60%); Class 4-very mild or no enzyme deficiency (60%); and Class 5-increased enzyme activity.

For the determination of hemoglobin concentration, a curve set will be programmed into calibration software where the Percent (%) Reflectance obtained by the meter software equals g/dL Hgb of the reference sample. For the determination of G6PDH activity, another curve set will also be programmed into the calibration software where the % Reflectance obtained by the meter software equals Units of G6PDH of the reference sample.

These values will be corrected for temperature as follows: (Units G6PDH)/(g/dL Hgb)×TFC, where TFC=Temperature Correction Factor.

In addition to the test strips, which in some embodiments are provided as a plurality of test strips in a vial kits and assays of the present invention may further comprise alcohol wipes, a plurality of lancets, as well as controls comprised, for example, of a preserved, polymeric solution spiked with G6PDH and hemoglobin.

The following non-limiting examples are provided to further illustrate the present invention.

EXAMPLES

Two significant considerations in the present invention include: (1) the lowest concentration level at which the Hgb and G6PDH can be detected with a high degree of reliability (sensitivity); and (2) the differential between various concentrations of both analytes (dynamic range) which can be distinguished from one another. In order to evaluate the Hgb and G6PDH assays of the present invention, titrations of Hgb and G6PDH were prepared and evaluated.

Example 1: Determination of Hgb Concentration in Human Whole Blood

An experiment was performed to investigate whether the invention described above is linear throughout the proposed analytical range.

A primary membrane working solution 1A comprising an aqueous buffered solution of 2% saponin and 1% Triton X-100 was prepared.

Four primary membranes inclusive of a spreading layer of hydrophilic mesh and a primary membrane (1A) namely: Ahlstrom HV plus; Pall Biodyne A 1.2 µM; Pall Biodyne A 5.0 µM; and Ahlstrom cellulose membrane 601; were impregnated with the primary working solution 1A and dried at 55° C. for 30 minutes.

A secondary membrane working solution 2A comprising 50 mM Tris buffer (Sigma-Aldrich) pH 7.8, 50 mM Sodium Nitrite (Sigma-Aldrich), 50 mM of sodium azide (Sigma-Aldrich), 0.2% Surfactant 10G (Fitzgerald Industries International) and 0.2% polyvinyl alcohol (Sigma-Aldrich) was prepared.

Secondary membrane 2A comprised of a 2.0 µM PES "NX" membrane from IPOC, or a 0.8 µM MMM membrane from Pall. These two membranes were immersed in the working solution 2A and dried at 55° C. for 30 minutes.

Tertiary membrane 3A, the optical membrane was an untreated BTS 0.05 µM membrane (Pall). Several studies revealed that an anisotropic membrane of small pore size helped remove cellular debris, eliminating background signal.

Whole blood was collected in EDTA, anticoagulant tubes, from a participant for this study. The whole blood was aliquoted into seven (1-mL) microcentrifuge tubes. The Hgb concentration was adjusted by removing serial amounts of plasma from 4 tubes with whole blood and then re-dispensing that plasma into several of the other 1-mL tubes with whole blood, to represent Hgb dilutions over the proposed analytical range of 3.0 to 24.0 g/dL Hgb. Each of the whole blood samples were assayed for g/dL Hgb using a reference instrument, the HemoCue Hb 301.

Figure 1:
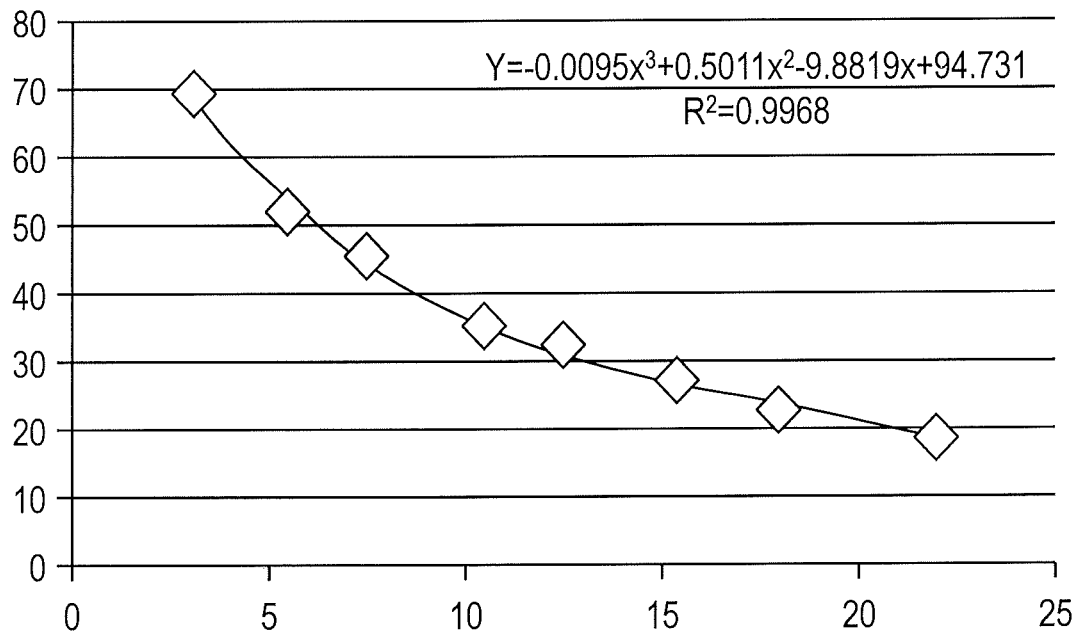
FIG. 1 is a graph comparing g/dL of hemoglobin in whole blood as measured by the Mission Plus Meter versus the percent reflectance (% R) obtained with the present invention.
Figure 2:
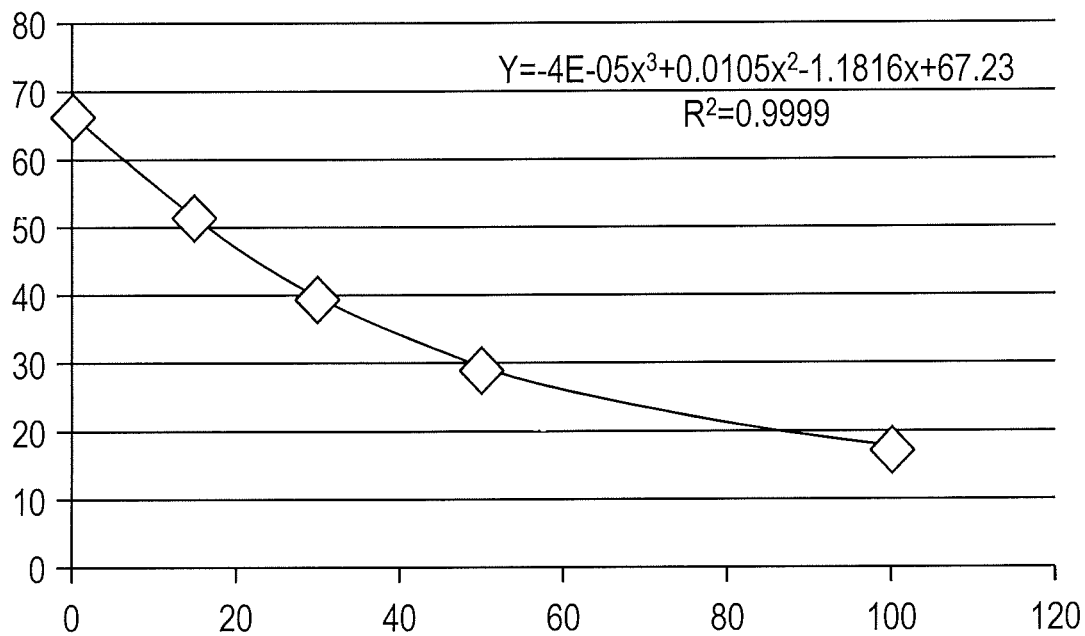
FIG. 2 is a graph comparing units/gram of spiked, known G6PDH levels in plasma versus the percent reflectance (% R) obtained with the present invention. The percent Reflectance was determined by a spectrophotometer.

The HemoCue Hb 301 g/dL values of the 8 diluted whole blood samples were as follows: (1) 2.75, (2) 5.5, (3) 7.5, (4) 10.5, (5) 12.5, (6) 15.4, (7) 18, and (8) 22 g/dL. To obtain a sample near the lower analytical limit of detection of the present invention (3 g/dL), sample 2 was diluted 1:1 with plasma to obtain a 3.25 g/dL sample. Thirty microliters were dispensed on the test strip (described above) and percent reflectance was recorded for each sample. Each sample was assayed in duplicate. The g/dL values obtained from the Hgb reference method were plotted against the percent reflectance from the in-house Hgb test strip. The glass fiber membrane lysed and captured cellular debris and was used to collect the data depicted in FIG. 1.

The data showed excellent agreement between the values obtained using the Acon Mission Plus meter and the reflectance values obtained from the in-house Hgb test strip.

The assay of the present invention reveals excellent linearity against the reference instrument across the analytical range. The device will require calibration against a reference instrument where Percent Reflectance (% R)=g/dL Hgb. The data reveals a very good delta and excellent precision for measuring g/dL Hgb. The sensitivity of the assay appears appropriate at 3.0 g/dL with an upper limit of 24.0 g/dL. This range can be changed to harmonize the requirements to the end user. The dynamic range can be changed by changing the porosity of the tertiary Membrane 3A.

Example 2: Determination of G6PDH in Spiked Plasma Samples

G6PDH was purchased from Calzyme Laboratories EC 1.1.1.49. Glucose-6-phosphate (G-6-P) was also purchased from Calzyme Laboratories, part number 046M0000. Diaphorase-1 was purchased from Nipro Medical Corporation. $NADP^+$ was purchased from Calzyme Laboratories, part number 218J0000. Nitro Blue Tetrazolium (NBT) salt was purchased from Sigma-Aldrich, part number N6875. Several iterations were carried out to test the immobilized concentrations of G-6-P, as well as with and without G-6-P, on the secondary Membrane 2B. In addition, several iterations were carried out to test the immobilized concentrations of diaphorase, $NADP^+$, and tetrazolium salt on a thin layer film format, reagent Membrane 3B, of the test strips. Both Membrane 2B and 3B were coated and dried at 55° C. for 20 minutes.

The tetrazolium chosen for the experiment was nitro blue tetrazolium chloride (NBT). NBT was dissolved in a methanol solution with polyvinyl alcohol. The rate of change in percent reflectance (% R) was measured at 565 nm to determine the optimal concentrations of all immobilized bioactive components. The samples were altered for both Hgb and spiked G6PDH plasma, encompassing the clinically significant range for both anemia and G6PDH deficiency. Percent reflectance (% R) was measured using a spectrophotometer. The data reveals excellent agreement with both G6PDH and Hgb dose response curves.

What is claimed is:

1. A test strip for simultaneous colorimetric quantification of glucose-6-phosphate dehydrogenase (G6PDH) and hemoglobin (Hgb) in a biological sample, said test strip comprising superimposed membrane layers comprising:
    a spreading layer capable of distributing or metering a biological sample across the surface of a primary membrane;
    a primary membrane, said primary membrane being in direct contact with the spreading layer so that a biological sample applied to the test strip flows transversely across the spreading layer and then migrates vertically or horizontally into the primary membrane;
    a secondary membrane for hemoglobin comprising a surfactant, an immobilizing mordant, sodium azide and sodium nitrite for producing azidomethemoglobin or a direct read of end-color of lysed red blood cells;
    a secondary membrane for G6PDH comprising a surfactant, a mordant, glucose-6-phosphate as a substrate, and sodium nitrite;

wherein said secondary membranes are not in direct contact with each other but are in direct contact with said primary membrane;

an optical reagent membrane for hemoglobin in direct contact with said secondary membrane for hemoglobin, said optical reagent membrane for hemoglobin comprising a surfactant and being capable of removing small particulate cellular debris and providing a uniform color across the surface of the membrane;

an optical reagent membrane for G6PDH in direct contact with said secondary membrane for G6PDH, said optical reagent membrane for G6PDH comprising a surfactant, an electron mediator, nicotinamide adenine dinucleotide phosphate (NADP$^+$), and a bio-reactive indicator generating a signal which is proportional to liberated G6PDH in the biological sample, wherein said optical membranes are horizontally segregated from each other, and wherein said test strip provides a quantitative analytical range of 0.03 to 25.0 units G6PDH/(gram/dL Hgb).

2. The test strip of claim 1 wherein the primary membrane is a digestive membrane capable of hemolyzing red blood cells.

3. The test strip of claim 1 wherein the primary membrane contains sodium nitrite or an oxidizing agent to convert ferrous iron ($Fe^{(2+)}$) to ferric iron ($Fe^{(3+)}$).

4. The test strip of claim 1, wherein the biological sample is whole blood, urine, or saliva.

5. The test strip of claim 1 wherein the biological sample is whole blood and the primary membrane comprises one or more hemolytic agents.

6. A test kit for simultaneous quantification of hemoglobin (Hgb) and glucose-6-phosphate dehydrogenase (G6PDH) in a biological sample, said test kit comprising the test strip as set forth in claim 1.

7. A method for simultaneous quantification of hemoglobin (Hgb) and glucose-6-phosphate dehydrogenase (G6PDH) in a biological sample, said method comprising applying a biological sample to the spreading layer of the test strip as set forth in claim 1 and reading the results of the test strip which are able to simultaneously quantify the levels of hemoglobin (Hgb) and glucose-6-phosphate dehydrogenase (G6PDH) in the biological sample.

8. The method of claim 7 further comprises obtaining and applying the biological sample directly from the patient.

9. The method of claim 7 wherein the biological sample is whole blood, saliva, or urine.

\* \* \* \* \*

UNITED STATES PATENT AND TRADEMARK OFFICE
CERTIFICATE OF CORRECTION

PATENT NO. : 11,041,860 B2  
APPLICATION NO. : 16/084700  
DATED : June 22, 2021  
INVENTOR(S) : Robert Harper Page 1 of 1

It is certified that error appears in the above-identified patent and that said Letters Patent is hereby corrected as shown below:

In the Specification

At Column 1, Line 14, add --This invention was made with government support under Grant Number AI129057 awarded by the National Institutes of Health. The government has certain rights in the invention.--

Signed and Sealed this  
Twenty-seventh Day of June, 2023

Katherine Kelly Vidal  
*Director of the United States Patent and Trademark Office*